(12) United States Patent
Hieronymi et al.

(10) Patent No.: US 8,115,018 B2
(45) Date of Patent: Feb. 14, 2012

(54) PROCESS FOR BROMINATING ALKYLTHIOPHENES

(75) Inventors: Antje Hieronymi, Köln (DE); Andreas Martin, Burscheid (DE); Witold Broda, Neunkirchen-Seelscheid (DE)

(73) Assignee: SALTIGO GmbH, Langenfeld (DE)

( * ) Notice: Subject to any disclaimer, the term of this patent is extended or adjusted under 35 U.S.C. 154(b) by 335 days.

(21) Appl. No.: 12/419,570

(22) Filed: Apr. 7, 2009

(65) Prior Publication Data

US 2009/0259053 A1    Oct. 15, 2009

(30) Foreign Application Priority Data

Apr. 11, 2008   (DE) .......................... 10 2008 018 485

(51) Int. Cl.
*C07D 333/28*   (2006.01)
(52) U.S. Cl. ........................................................ 549/81
(58) Field of Classification Search ...................... 549/81
See application file for complete search history.

(56) References Cited

FOREIGN PATENT DOCUMENTS
CN         101 045 723    * 10/2007

OTHER PUBLICATIONS

Higuchi Hiroyuki, et al.; "Synthesis and Properties of Alpha . , . Omega—Disubstituted Oligo (3-Hexylthiophene)s and Oligothienoquinonoids in Head-to-Head Orientation"; Bulletin of the Chemical Society of Japan, Tokyo, JP, Bd. 68, No. 8, Jan. 1, 1995, pp. 2363-2377, XP008070697.
Brandsma, et al.; Synlett. 1988, p. 890.
Burrell, et al.; J. Org. Chem. 2003, p. 8974.

* cited by examiner

*Primary Examiner* — Andrew D Kosar
*Assistant Examiner* — Karen Cheng
(74) *Attorney, Agent, or Firm* — Michael A. Miller

(57) ABSTRACT

What is described is a process for brominating alkylthiophene, in which an alkylthiophene of the general formula (I)

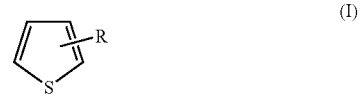

(I)

where
R is a branched or unbranched alkyl radical having 1 to 12 carbon atoms
is contacted with stoichiometric amounts of HBr and $H_2O_2$, optionally in the presence of a solvent.

5 Claims, No Drawings

PROCESS FOR BROMINATING ALKYLTHIOPHENES

The invention provides a process for brominating alkylthiophenes. Bromination is understood to mean tri-, di- or monobromination.

Alkylthiophenes, especially 3-hexylthiophene, are used to prepare organic semiconductive polymers which are used in electronic components, for example semiconductors or solar cells. A precursor for preparation of these polyalkylthiophenes is the corresponding mono or dibromo derivatives.

The bromination of alkylthiophenes (usually the dibromination of 3-hexylthiophene) is, according to the present standard, performed with the aid of elemental bromine or using N-bromosuccinimide (NBS).

In 1988, Brandsma et al. (Synlett. 1988, 890) published the monobromination of unsubstituted thiophene with excess HBr and substoichiometric amounts of hydrogen peroxide. The solvent used for this reaction was diethyl ether, and that used for the workup n-pentane. The dibromination of thiophene is described in the same article and is performed with the aid of HBr/$Br_2$ (likewise in diethyl ether). Burrell et al. (J. Org. Chem. 2003, 8974) describe the bromination of 3-formylthiophene with HBr/hydrogen peroxide.

At the time of the invention, there was thus still a need for a process for brominating alkylthiophenes which avoids the use of toxic bromine or expensive brominating reagents. In addition, the space-time yield of this reaction is also in need of improvement.

It was therefore an object of the present invention to find a process for brominating alkylthiophenes, which avoids the use of elemental bromine ($Br_2$) or expensive brominating reagents such as N-bromosuccinimide.

It has now been found in accordance with the invention that the bromination of alkylthiophenes can also be effected through the use of stoichiometric amounts of hydrogen bromide and hydrogen peroxide, without any need to add a solvent.

The invention therefore provides a process for brominating alkylthiophene, in which an alkylthiophene of the general formula (I)

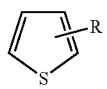

(I)

where
R is a branched or unbranched alkyl radical having 1 to 12 carbon atoms is contacted with stoichiometric amounts of HBr and $H_2O_2$, optionally in the presence of a solvent.

The bromination of the alkylthiophene can be performed to completion (tribromination) or as a mono- or dibromination. Preference is given to performing the bromination as a dibromination, which means that 2 carbon atoms of the thiophene skeleton are brominated. The degree of bromination is controlled by the appropriate stoichiometric use of HBr and $H_2O_2$. A stoichiometric amount is understood to mean the amount of HBr and $H_2O_2$ which are required to prepare the mono- or dibromo product.

Typically, the HBr is used in the form of an aqueous HBr solution having a content of 10 to 62% by weight of hydrobromic acid, preferably 30 to 60% by weight, more preferably 48% of hydrobromic acid. The $H_2O_2$ used is an aqueous $H_2O_2$ solution having a content of 25 to 35% by weight of hydrogen peroxide, preferably 30-35% by weight of hydrogen peroxide.

The reaction time within which alkylthiophene is contacted with HBr and $H_2O_2$ is typically between 1 and 36 hours, preferably between 5 and 10 hours.

The reaction temperature is typically within the range between −10 and +80° C., preferably between −5 and +50° C., more preferably 45° C.

Typically, the process according to the invention is performed without addition of a further solvent. If desired, it is, however, also possible to add a solvent, for example diethyl ether or other ethers or chlorinated solvents. In this case, the solvent can be removed again from the brominated end product after the reaction has ended by customary separation methods, for example distillation.

The process according to the invention can be used to brominate all positional isomers of alkylthiophene. Preference is given, however, to using 3-alkylthiophene having 1 to 12 carbon atoms in the alkyl chain in the process according to the invention. Particular preference is given to using 3-hexylthiophene for bromination in the process according to the invention, preferably to prepare the mono- or dibromo product.

The examples which follow are intended to further illustrate the invention, but without restricting its scope.

EXAMPLES

Example 1

Comparative 75 g of 3-hexylthiophene were initially charged in 375 ml of THF. At RT, 167 g of NBS were added in portions within 4 h. After continuing to stir for 17 hours, 16 g of NBS and 25 ml of THF were metered in and stirred for a further 17 h. The mixture was filtered and the solvent was distilled off. The crude product (2,5-dibromo-3-hexylthiophene) had a purity of 91.7%; the yield of the crude product was 83%.

Example 2

Inventive 338 g of 3-hexylthiophene were initially charged with 1070 g of 48% hydrobromic acid. The mixture was cooled to −5° C. and admixed with 400 g of 34% hydrogen peroxide over a period of 7 h. Within 16 h, the mixture was warmed to 20° C. The phases were separated. The crude product (2,5-dibromo-3-hexylthiophene) had a purity of 96.9%; the yield of the crude product was 97%.

Example 3

Inventive 343 g of hexylthiophene were initially charged with 674 g of 48% hydrobromic acid. The mixture was warmed to 37° C. and admixed with 454 g of 30% hydrogen peroxide over a period of 7 h. The mixture was stirred at 45° C. overnight. Then 21 g of 40% sodium bisulphite solution were added and the phases were separated. The crude product had a purity of 90.7%; the yield of the crude product (2,5-dibromo-3-hexylthiophene) was 88%.

The invention claimed is:

1. A process for brominating alkylthiophene, in which an alkylthiophene of the general formula (I)

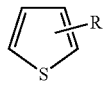 (I)

where
R is a branched or unbranched alkyl radical having 1 to 12 carbon atoms
is contacted with stoichiometric amounts of HBr and $H_2O_2$, wherein the HBr is an aqueous HBr solution having a content of 10 to 62% by weight of hydrobromic acid and wherein $H_2O_2$ is an aqueous $H_2O_2$ solution having a content of 25 to 35% by weight of hydrogen peroxide and wherein no further solvent is added.

2. The process according to claim 1, wherein the bromination is performed as a mono- or dibromination.

3. The process according to claim 1, wherein the alkylthiophene of the general formula (I) is contacted with the HBr and the $H_2O_2$ at a temperature in the range of −10 to +80° C.

4. The process according to claim 1, wherein the alkylthiophene of the general formula (I) is a 3-alkylthiophene.

5. The process according to claim 1, wherein the alkylthiophene is 3-hexylthiophene and the product is 2-bromo-3-hexylthiophene or 2,5-dibromo-3-hexylthiophene.

* * * * *